(12) United States Patent
Li

(10) Patent No.: US 11,523,789 B2
(45) Date of Patent: Dec. 13, 2022

(54) SYSTEM AND METHOD FOR USING NON-CONTRAST IMAGE DATA IN CT PERFUSION IMAGING

(71) Applicant: Wisconsin Alumni Research Foundation, Madison, WI (US)

(72) Inventor: Ke Li, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 250 days.

(21) Appl. No.: 16/901,537

(22) Filed: Jun. 15, 2020

(65) Prior Publication Data

US 2021/0386393 A1 Dec. 16, 2021

(51) Int. Cl.
*A61B 6/00* (2006.01)
*G06T 11/00* (2006.01)
(Continued)

(52) U.S. Cl.
CPC ............ *A61B 6/5241* (2013.01); *A61B 6/032* (2013.01); *A61B 6/4452* (2013.01); *A61B 6/501* (2013.01);
(Continued)

(58) Field of Classification Search
CPC ..... A61B 6/507; A61B 6/5217; A61B 6/5241; A61B 6/032; A61B 6/5258; A61B 6/504; A61B 6/481; A61B 6/501; A61B 6/4452; A61B 6/5235; A61B 6/5205; A61B 6/035; A61B 6/466; A61B 6/503; A61B 6/545; A61B 6/02; A61B 6/461; A61B 6/54; A61B 6/50; A61B 6/482; A61B 6/469; A61B 6/488; A61B 6/5223; A61B 6/03; A61B 6/4241; A61B 6/5211; A61B 6/4014; A61B 6/4028; A61B 6/4417; A61B 6/487; A61B 6/542; A61B 2576/026; A61B 5/02007; A61B 6/5247; A61B 6/037; A61B 5/02028; A61B 5/0035; A61B 5/055; A61B 5/026; A61B 6/5264; A61B 5/021; A61B 5/4884; A61B 5/7285; A61B 5/0285; A61B 5/0022; A61B 5/7278; A61B 5/0275;
(Continued)

(56) References Cited

U.S. PATENT DOCUMENTS

2002/0161292 A1* 10/2002 Wintermark ......... A61B 5/4076
                                                600/407
2016/0180042 A1* 6/2016 Menon .................... G16H 50/20
                                                705/2
(Continued)

OTHER PUBLICATIONS

Li, Ke and Chen, Guang-Hong, Noise characteristics of CT perfusion imaging: How does noise propagate from source images to final perfusion maps?, Proc SPIE 9783, Medical Imaging 2016: Physics of Medical Imaging, 978310, Mar. 22, 2016.
(Continued)

*Primary Examiner* — Irakli Kiknadze
(74) *Attorney, Agent, or Firm* — Quarles & Brady LLP

(57) ABSTRACT

A system and method for generating a parametric map of a subject's brain includes receiving non-contrast computed tomography (NCCT) imaging data and receiving computed tomography perfusion (CTP) data. The method further includes creating a baseline image by utilizing the NCCT data and generating a parametric map using the CTP data and the baseline image.

17 Claims, 2 Drawing Sheets

(51) Int. Cl.
*G06T 7/00* (2017.01)
*A61B 6/03* (2006.01)

(52) U.S. Cl.
CPC .......... *A61B 6/507* (2013.01); *A61B 6/5258* (2013.01); *G06T 7/0012* (2013.01); *G06T 11/005* (2013.01); *G06T 2207/30016* (2013.01); *G06T 2207/30104* (2013.01)

(58) Field of Classification Search
CPC ... G06T 7/0012; G06T 11/005; G06T 11/006; G06T 2207/30016; G06T 2207/30104; G06T 2211/421; G06T 7/0016; G06T 7/38; G06T 2211/408; G06T 2207/30061; G06T 2207/10081; G06T 5/50; G06T 7/11; G06T 11/008; G06T 7/32; G06T 7/0014; G06T 11/003; G06T 2207/10116; G06T 2207/20081; G06T 2207/20224; G06T 2207/30101; G06T 15/08; G06T 15/20; G06T 17/00; G06T 3/60; G06T 5/002; G06T 7/20; G06T 2210/41; G06T 2211/404; G16H 50/20; G16H 30/00; G16H 50/30; G16H 30/40; G16H 10/60; A61N 5/1037; G06F 30/20

USPC .............................................. 378/4, 19, 62
See application file for complete search history.

(56) References Cited

U.S. PATENT DOCUMENTS

2017/0086772 A1* 3/2017 Vaz ................ A61B 6/486
2020/0375564 A1* 12/2020 Freiman .............. A61B 6/5217

OTHER PUBLICATIONS

Li, Ke and Chen, Guang-Hong, Dependence of quantitative accuracy of CT perfusion imaging on system parameters, Proc of SPIE 10132, Medical Imaging 2017: Physics of Medical Imaging, vol. 10132, Mar. 9, 2017.

Morelli, N., Rota, E., Michieletti, E., and Guidetti, D., The "Vexata Quaestio" on Lacunar Stroke: The Role of CT Perfusion Imaging, AJNR Am J Neuroradiol, 38(2), E11-E12, Feb. 1, 2017.

Gonzalez, Ramon Gilberto, Current State of Acute Stroke Imaging, Stroke, Nov. 2013, pp. 3260-3264.

* cited by examiner

SYSTEM AND METHOD FOR USING NON-CONTRAST IMAGE DATA IN CT PERFUSION IMAGING

STATEMENT REGARDING FEDERALLY SPONSORED RESEARCH

This invention was made with government support under EB021183 awarded by the National Institutes of Health. The government has certain rights in the invention.

CROSS-REFERENCE TO RELATED APPLICATIONS

N/A

BACKGROUND

The present disclosure relates to systems and methods to produce images or maps of a subject using computed tomography data. More particularly, the present disclosure provides systems and methods for producing images and/or maps of a subject with reduced noise levels/increased contrast to noise ratios.

In computed tomography (CT) systems, an x-ray source projects a beam that is collimated to lie within an X-Y plane of a Cartesian coordinate system, termed the "imaging plane." The x-ray beam passes through the object being imaged, such as a medical patient, and impinges upon an array of radiation detectors. The intensity of the radiation received by each detector element is dependent upon the attenuation of the x-ray beam by the object and each detector element produces a separate electrical signal that relates to the attenuation of the beam. The linear attenuation coefficient is the parameter that describes how the intensity of the x-rays changes when passing through an object.

To achieve this process, a source and detector array are rotated on a gantry within the imaging plane and around the object so that the projection angle at which the x-ray beam intersects the object constantly changes. A group of x-ray attenuation measurements from the detector array at a given angle is referred to as a "view" and a "scan" of the object. These views are collected to form a set of views made at different angular orientations during one or several revolutions of the x-ray source and detector. In a two dimensional (2D) scan, data are processed to construct an image that corresponds to a 2D slice taken through the object. The prevailing method for reconstructing an image from 2D data is referred to in the art as the filtered backprojection (FBP) technique. This process converts the attenuation measurements from a scan into integers called "CT numbers" or "Hounsfield units", which are used to control the brightness of a corresponding pixel on a display.

CT imaging has become the gold standard driving clinical care in a wide variety of clinical applications. As just one example, cerebral CT perfusion (CTP) imaging is widely used to diagnose acute ischemic stroke and identify patients who are most likely to benefit from endovascular reperfusion therapy, because parametric CTP maps can assist physicians to identify the existence of hypoperfused but salvageable tissue upon reperfusion, and to differentiate this tissue from irreversibly damaged tissue (ischemic core) for which reperfusion is futile or even lethal. CTP is usually performed together with a non-contrast head CT (NCCT) for ruling out intracranial hemorrhage and a CT angiography (CTA) for estimating the location of thrombus. This CT imaging package of CTP imaging and NCCT imaging is carried out in less than 10 minutes in the same imaging suite and bed position, which is highly efficient compared with other imaging protocols, such as a combination of CT and magnetic resonance imaging (MRI) imaging studies. Even for post stroke treatment follow-up or imaging work-ups of chronic stroke and other neurological diseases, a CTP study is often prescribed together with NCCT imaging to provide more comprehensive and mutually complementary diagnostic information.

Despite the clinical utility, the current CTP imaging technology still faces a major challenge reflected by poor contrast-to-noise ratio (CNR) of parametric CTP maps. This low CNR can hinder reliable or consistent stroke diagnosis for individual patients. For example, one clinical study (Gonzalez, "Current State of Acute Stroke Imaging," Stroke 44, 3260-3264, 2013.) found that the CNR of an ischemic core in CTP maps could be smaller than "1", while the same core identified in diffusion weighted MRI images demonstrated a CNR of more than "8". Observations such as this motivated researchers to conclude that "the inherently poor CNR of CTP derived images is the fundamental flaw in the technique." Morelli N, Rota E, Michieletti E, Guidetti D. The "Vexata Quaestio" on lacunar stroke: the role of CT perfusion imaging. AJNR Am J Neuroradiol. 2017; 38(2): E11-2.

Thus, there is a continuing need for new and improved imaging techniques that provide clinicians with robust and consistent information for clinical use, particularly, in critical care situations, such as head or brain imaging, including situations involving stroke.

SUMMARY

The present disclosure overcomes the aforementioned drawbacks by providing systems and methods for improving CT perfusion studies by reducing the noise in baseline image(s) by utilizing non-contrast CT image data to create the baseline image(s). For example, a non-contrast CT image volume data and CT perfusion data can be combined or "fused" to generate baseline image(s), such that the baseline image(s) have a higher CNR than delivered by the CT perfusion data, which substantially improves overall CNR of parametric maps generated from the CT perfusion data. For example, thee improved CNR is substantially greater than increased dose applied to the CT perfusion data could yield and/or without subjecting the patient to further dose because the non-contrast CT data is available. That is, the present disclosure recognizes that the noise of a Cerebral Blood Volume (CBV) map is strongly influenced by the noise level of the baseline CT image for both deconvolution and non-deconvolution-based CTP techniques. With this realization, the present disclosure provides systems and methods for improving CT perfusion studies by reducing the noise in baseline images.

In accordance with one aspect of the disclosure, a medical imaging system is provided that includes an x-ray source configured to deliver x-rays to an imaging patient. The medical imaging system also includes a detector array configured to receive the x-rays after passing the imaging patient and a controller configured to rotate the x-ray source and the detector array about the imaging patient as the x-ray source delivers the x-rays to the imaging patient and the detector array receives the x-rays. The system further includes a computer system configured to control operation of the x-ray source and the detector array to perform a non-contrast computed tomography (NCCT) imaging acquisition to acquire NCCT data. The computer system is further configured to control operation of the x-ray source and the detector array to perform a computed tomography perfusion (CTP) imaging acquisition to acquire CTP data, create a baseline image using the NCCT data, and generate a parametric map using the CTP data and the baseline image.

In accordance with another aspect of the disclosure, a method is provided for generating a parametric map of a subject's brain. The method includes receiving non-contrast computed tomography (NCCT) imaging data and receiving computed tomography perfusion (CTP) data. The method further includes creating a baseline image using the NCCT data and generating a parametric map using the CTP data and the baseline image In accordance with one other aspect of the disclosure, a computer system is provided that is configured to generate a parametric map of a subject's brain. The computer system includes a memory storing or having access to store non-contrast computed tomography (NCCT) imaging data acquired from the subject and computed tomography perfusion (CTP) data acquired from the subject. The computer system also includes a processor having access to the memory and configured to create a baseline image using the NCCT data and generate a parametric map using the CTP data and the baseline image.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
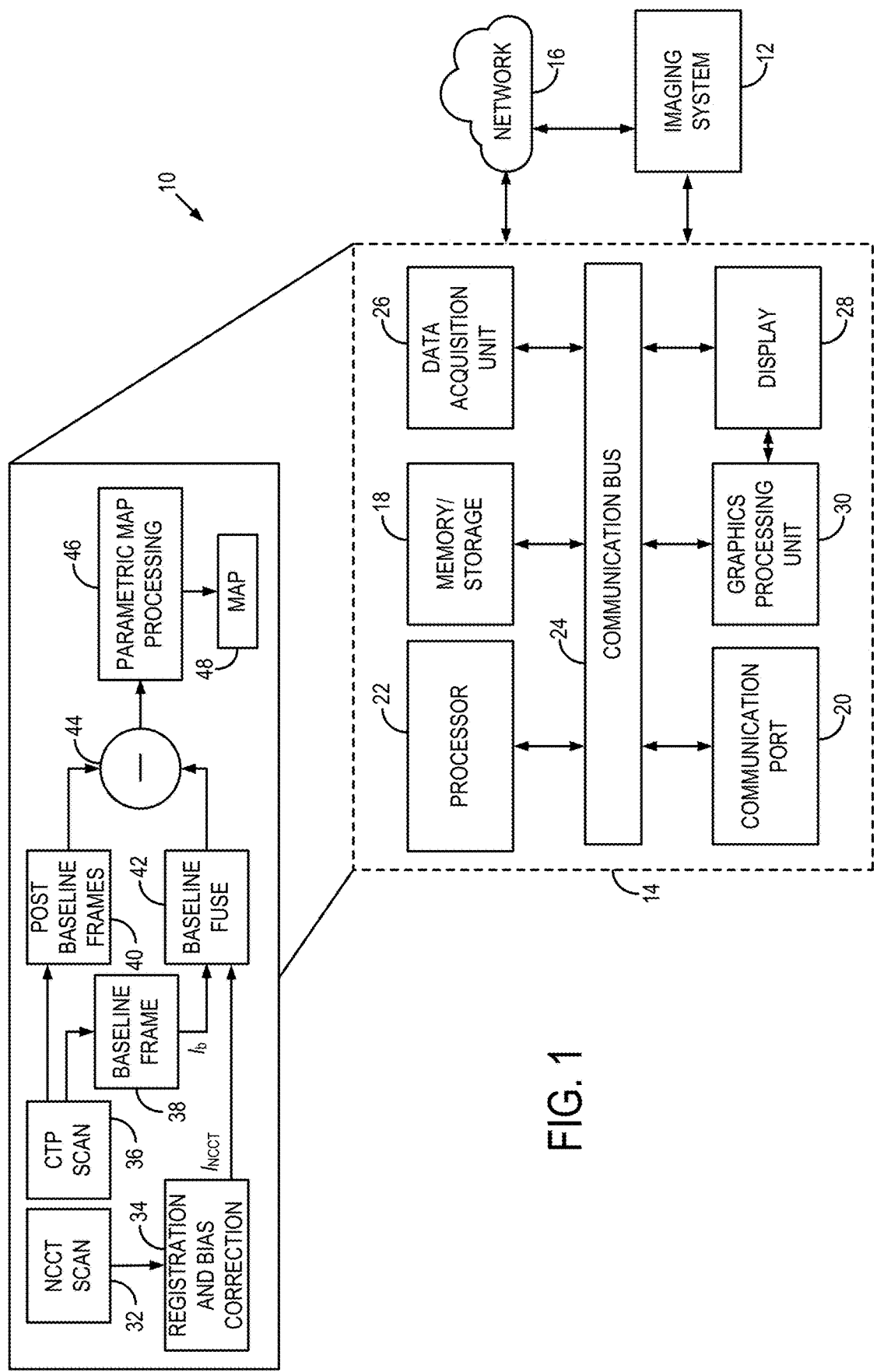
FIG. 1 is a schematic diagram of an example computer system that can be configured to implement the methods described herein.

Though low CNR in CTP data and the resulting CNR of an ischemic core in CTP maps has been identified, the conclusion of researchers studying the phenomenon was that the low CNR resulted from a "fundamental flaw" in CTP. Thus, some have turned to other imaging modalities, such as MRI and diffusion weighted imaging (DWI), to overcome this "fundamental flaw."

Instead of a resignation to a "fundamental flaw" in CT imaging and CTP data, the present disclosure analyzed and considered the origin of the poor CNR in CTP data. To identify the fundamental origin of the poor CNR, a first-principles analysis was performed to demonstrate that the root cause of the poor CNR of CTP maps is the poor CNR of CTP source images. In particular, the CNRs of some CTP maps such as cerebral blood volume (CBV) are predominately determined by the baseline (or mask) CT images. Thus, the present disclosure determined that reducing the baseline image noise can be effective in improving the CNR of CTP maps. Thus, as will be described, the present disclosure provides systems and methods to reduce the noise of baseline images and improve the CNR of CBV maps. In one non-limiting example, systems and methods are provided to use NCCT image data to produce baseline (or mask) CT images for use in producing CTP maps, which manifest in substantially higher CNR than CTP maps or images produced using traditional techniques.

Parametric cerebral perfusion imaging is based on the following convolution relationship that can be derived using the indicator-dilution theory:

$$C_{tis}(t) = C_a(t) \otimes k(t), \quad (1);$$

in which $C_{tis}(t)$ and $C_a(t)$ denote temporal iodine concentrations curves in brain tissue and a feeding cerebral artery, respectively; $\otimes$ denotes the convolution operator; $k(t)$ denotes the so-called flow-scaled residue function from which CBV, CBF, and MTT can be solved. Taking CBV as an example, it is related to $k(t)$ by:

$$CBV = \frac{\kappa}{\rho} \int_0^\infty k(t)dt, \quad (2);$$

where $\rho$ is the density of brain tissue, and $\kappa$ is the ratio between the arterial and capillary hematocrits. The goal of cerebral perfusion imaging is to estimate CBV and other perfusion parameters, either by deconvolving $C_{tis}(t)$ with $C_a(t)$, or using other non-deconvolution-based methods. No matter which method is employed, knowledge of $C_{tis}(t)$ and $C_a(t)$ is needed for the analysis.

In CT-based perfusion imaging, iodine concentration curves $C_{tis}(t)$ and $C_a(t)$ are estimated based on the increment (i.e., enhancement) of CT number as:

$$C_{tis}(\vec{x},t) = \alpha[I(\vec{x},t) - I_b(\vec{x})] = \alpha \Delta I(\vec{x},t), \quad (3); \text{ and}$$

$$C_a(t) = \alpha[I(\vec{x},t) - I_b(\vec{x}_a)] = \alpha \Delta I(t), \quad (4);$$

where $\vec{x}$ and $\vec{x}_a$ denote spatial locations of brain tissue and the artery, respectively. $I_b$ denotes the CT number of the baseline CT image acquired prior to the wash-in of iodine, and $\alpha$ is a global scaling factor that is present on both sides of Eq. (1) and can, therefore, be removed. Thus, the statistical properties of the final perfusion maps depend on the quality of not only $I(t)$, but also $I_b$. Taking CBV as an example:

For non-deconvolution-based CTP systems, the noise variance of CBV is given by:

$$\sigma^2_{CBV} \approx \left(\frac{\kappa \Delta t}{\rho \beta}\right)^2 (N\sigma^2 + N^2 \sigma_b^2), \quad (5);$$

where N denotes the total number of post-baseline image frames, $\beta = \Delta I_a(t)dt$, $\sigma^2$ denotes the noise variance of post-baseline CT images, and $\sigma_b^2$ denotes the noise variance of the baseline image. Since $N^2 \gg N$, the noise of non-deconvolution-based CTP systems is dominated by the baseline noise.

For deconvolution-based CTP systems, the convolution operation in Eq. (1) can be expressed using the following matrix-vector representations:

$$c = Ak, \quad (6);$$

where c and k are the vectorized forms of $\Delta I(t)$ and $k(t)$, respectively. Matrix A is constructed from $\Delta I_a(t)$ as follows:

$$A \triangleq \begin{bmatrix} I_a(t_1) & 0 & \cdots & 0 \\ I_a(t_2) & I_a(t_1) & \cdots & 0 \\ \vdots & \vdots & \ddots & \vdots \\ I_a(t_N) & I_a(t_{N-1}) & \cdots & I_a(t_1) \end{bmatrix}. \quad (7)$$

One approach to estimate k is to perform the singular value decomposition (SVD) of matrix A to help estimate its pseudo-inverse matrix, together with a Tikhonov regularizer to suppress the contribution of smaller singular values of A to the deconvolution results. It can be proved that the solution of the SVD+Tikhonov based deconvolution method is equivalent to the following closed-form solution:

$$k = B^T c, \text{ where } B =: A^T (A^T A + \lambda^2 I)^{-1} \quad (8);$$

and I is an N×N identity matrix. From k, CBV can be calculated using Eq. (2). The noise variance of the resulting CBV map is given by:

$$\sigma_{CBV}^2 \approx \left(\frac{\kappa \Delta t}{\rho}\right)^2 [\sigma^2 u^T B^T B u + \sigma_b^2 u B^T U B u] = \quad (9);$$
$$\left(\frac{\kappa \Delta t}{\rho}\right) \left[\sigma^2 \sum_{i=1}^{N} \sum_{j=1}^{N} \sum_{k=1}^{N} B_{ki} B_{kj} + \sigma_b^2 \left(\sum_{i=1}^{N} \sum_{j=1}^{N} B_{ij}\right)^2\right],$$

where u is an N×1, all-one matrix. Because $N^3$ summation terms in $(\Sigma_i \Sigma_j \Sigma_k B_{ki} B_{kj})$ is only a small subset of the $N^4$ summation terms in $(\Sigma_i \Sigma_j \Sigma_k B_{ij})^2$, the weight on the baseline noise $\sigma_b^2$ is much larger than the weight on $\sigma^2$. Thus, the present disclosure recognizes that the noise of a CBV map is strongly influenced by the noise level of the baseline CT image for both deconvolution and non-deconvolution-based CTP techniques.

With this realization, the present disclosure provides systems and methods for improving CT perfusion studies by reducing the noise in baseline images. One technique for reducing noise in CT images or imaging data is to acquire more baseline frames and take an average of these frames. However, doing so increase the radiation dose to the patient. This is particular problematic in clinical situations like stroke diagnosis and assessment where there is a need for multiple studies to be performed together and, thus, there is a total radiation budget that must be managed. That is, the total radiation budget of a clinical CTP exam is restricted and, thus, the baseline frames and the associated ionizing exposure can't be arbitrarily increased simply to improve CNR in the baseline images. Any increase in exposure/dose to increase CNR in one area, comes at the expense of CNR in another area to maintain the same total exposure/dose.

One dose modulation scheme that increases exposure for the baseline frames and decreases exposure for the non-baseline frames quantitatively relates the quantification accuracy of parametric perfusion parameters with CTP acquisition and postprocessing parameters. See Li K. et al., "Dependence of quantitative accuracy of CT perfusion imaging on system parameters" Proc. SPIE 10132, 101320D, 2017. However, using this technique, the exposure reduction in non-baseline frames can degrade the image quality of other perfusion maps such as time-to-peak (TTP), which is more dependent on the post-baseline frames. This is because, presumably, the extra exposure for baseline images comes at the expense of reduced exposure for non-baseline images.

Instead, the present disclosure provides a system and method that leverages the low-noise feature of NCCT images to decrease the baseline image noise, without increasing the post-baseline image noise. The system and method recognize that the non-contrast head CT has a much lower noise to facilitate the evaluation of subtle change in brain parenchyma's attenuation signal. In just one, non-limiting example, the NCCT image maybe acquired at a radiation dose level (quantified by $CTDI_{vol}$) of approximately 50 mGy, whereas the radiation dose for each CTP time frame may be about 13 mGy.

Referring now to FIG. 1, a block diagram of an example system 10 is provided that can be configured to carry out techniques, methods, and processes accordance with the present disclosure. The system may include an imaging system 12 that is coupled to a computer system 14. The coupling of the imaging system 12 to the computer system 14 may be a direct or dedicated network connection, or may be through a broad network 16, such as an intranet or the Internet.

The computer system 14 may be a workstation integrated with or separate from the medical imaging systems 12 or a variety of other medical imaging systems, including, as non-limiting examples, any of a variety of different computed tomography (CT) systems, such as will be described. Furthermore, the computer system 14 may be a workstation integrated within the medical imaging system 12 or may be a separate workstation or mobile device or computing system. To this end, the following description of particular hardware and configurations of the hardware of the example computer system 14 is for illustrative purposes. Some computer systems may have varied, combined, or different hardware configurations.

Medical imaging data acquired by the medical imaging system 12 or other imaging system can be provided to the computer system 14, such as over the network 16 or from a memory or storage 18. To this end, the computer system 14 may include a communications port or other input port (wired or wireless) 20 for communication with the network 16 and system coupled thereto.

In some configuration, computer system 14 may include one or more processing systems or subsystems 22. That is, the computer system 14 may include one or more physical or virtual processors. The processor 22 may communicate with other systems via a communications bus 24. As an example, the communication bus 24 can be a group of wires, or a hardwire used for switching data between the peripherals or between any component. The communication bus 24 may provide access to an integrated data acquisition unit 26. On the other hand, if the computer system 14 is integrated with the imaging system 12, the data acquisition unit 26 may form part of the imaging system 12.

The computer system 14 may also include or be connected to a display 28. The computer system 14 may include a graphics processing unit (GPU) 30. The display 28 may be a monitor connected to the computer system 14 or may be integrated with the computer system 14, such as in portable computers or mobile devices, or integrated or form part of the imaging system 12.

As will be further described, in operation, the computer system 14 or processor 22 of the computer system (and/or GPU 30 or other processor systems) is configured to carry out a method that leverages the low-noise feature of NCCT images to decrease the baseline image noise, without increasing the post-baseline image noise. In particular, at process block 32, an NCCT image volume is acquired using the medical imaging system 12. At process block 24, initial registration and bias correction is performed so that the NCCT image volume can be registered to a CTP baseline image volume acquired via a CTP scan at process block 36, again, using the medical imaging system 12. In particular, a baseline CTP image is selected at process block 38 from the CTP scan data acquired at process block 36, while post-baseline frames acquired from the CTP scan at process block 36 are passed forward at process block 40.

It is possible to compensate for the possible discrepancy between the CT number of brain parenchyma in the NCCT image data acquired via the NCCT scan at process block 34 and the CTP baseline image reflected at process block 38. Since NCCT scan 32 and the CTP scan 36 are performed during the same patient visit and with the same patient position, their registration generally not a substantial challenge. For the possible discrepancy in CT number (for parenchyma only; bone is irrelevant in the final CTP map) between NCCT scan 32 and CTP baseline image 38, a global offset-based method can be used at process block 34, although more complex algorithms can also be used to further mitigate any discrepancy. Regarding bias correction, this is performed at process block 34 by recognizing that, even under the same kV, the existence of a mAs-dependent CT number bias could lead to such a discrepancy, which can be corrected based on an experimentally validated bias model.

With these small corrections, the NCCT image volume and CTP baseline images can be combined or "fused" at process block 42, whereby the fused baseline image, $I'_b$, is given by:

$$I'_b = w I_{NCCT} + (1-w) I_b, \quad (10);$$

where $I_{NCCT}$ is the image delivered at process block 34, $I_b$ is the original baseline frame from process block 38, w is a weighting factor that can be chosen so that the noise variance of $I'_b$ is minimized, namely, $\arg\min_w \{w^2 \sigma_{NCCT}^2 + (1-w)^2 \sigma_b^2\}$. The solution for the optimal value of w is then given by:

$$w = \frac{\sigma_b^2}{\sigma_{NCCT}^2 + \sigma_b^2}, \quad (11).$$

With this weighting factor, the noise variance of $I'_b$ is:

$$\sigma_{b'}^2 = \left(\frac{\sigma_{NCCT}^2}{\sigma_{NCCT}^2 + \sigma_b^2}\right) \sigma_b^2 \leq \sigma_b^2, \quad (12).$$

That is, the baseline fused images can be subtracted 44 from the post-baseline frames provided at process block 40. These difference images can then be processed at block 46 to produce CBV maps 48 generated with reduced noise variance and increased CNR imparted to the CTP-based maps by imparting the higher-quality (higher CNR) from the NCCT scan 32 into the baseline frame 38 via the baseline fusing 42. That is, based on Eqs. (5) and (9), using the NCCT-assisted baseline image $I'_b$ with a reduced noise variance can effectively improve the image quality of maps 38 and/or indication of CBV.

Advantageously, the systems and methods provided herein can be compatible with existing CTP post-processing techniques and software, thereby, controlling interruption to established clinical workflows. For example, the systems and methods provided herein do not require proprietary reconstruction algorithms or fundamental reimagining of deconvolution algorithms.

As explained, the present disclosure recognizes that, for both deconvolution- and non-deconvolution-based cerebral CT perfusion systems, the noise of CBV has a more significant dependence on the baseline frame compared to post-baseline frames. Therefore, reducing the baseline image noise can effectively improve the CBV image quality. The above-described approach reduces the baseline noise by utilizing the comparatively higher-quality of non-contrast head CT images (NCCT images) that are almost always acquired prior to the CTP scan. The above-described method introduces no or minimal interruption to current clinical workflows, and does not degrade the quality of other perfusion maps or introduce additional radiation dose to the patient.

Figure 2A:
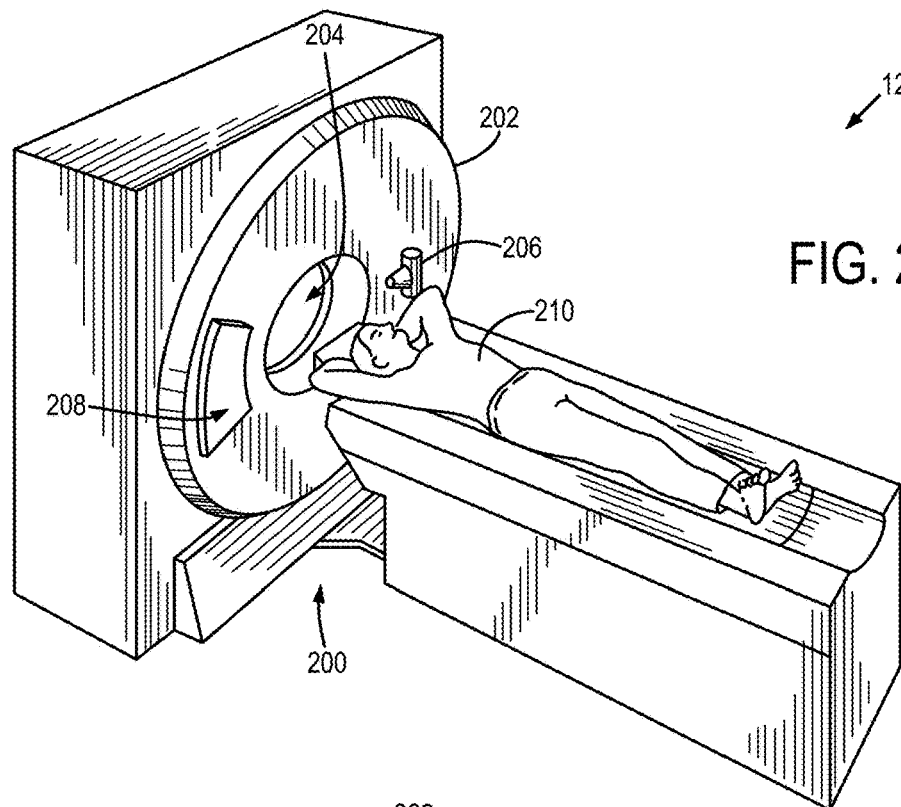
FIG. 2A is a perspective view of an example of an x-ray computed tomography (CT) system for use with the systems and methods of the present disclosure.
Figure 2B:
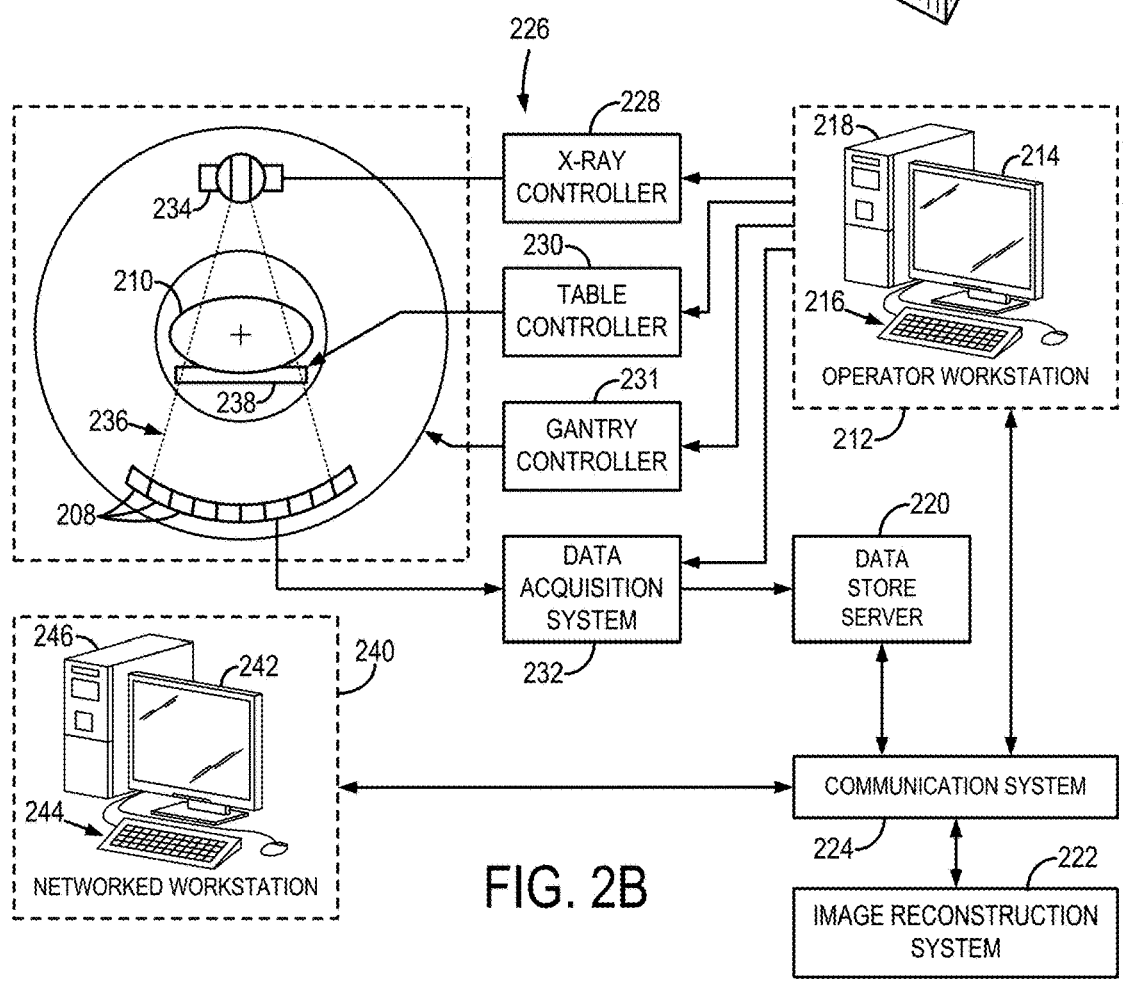
FIG. 2B is a block diagram of a CT system, such as illustrated in FIG. 2A.

The above-described systems and methods may utilize any of a variety of CT systems. For example, the above-described systems and methods may be used with so-called fixed-gantry CT systems, or other CT systems, such as a so-called "C-arm" x-ray imaging systems. Referring to FIGS. 2A and 2B, one example of the imaging system 12 may include a fixed-gantry CT system 200, which includes a gantry 202 that forms a bore 204 extending therethrough. In particular, the gantry 202 has an x-ray source 206 mounted thereon that projects a fan-beam, or cone-beam, of x-rays toward a detector array 208 mounted on the opposite side of the bore 204 through the gantry 202 to image the subject 210.

The CT system 200 also includes an operator workstation 212, which typically includes a display 214; one or more input devices 216, such as a keyboard and mouse; and a computer processor 218. The computer processor 218 may include a commercially available programmable machine running a commercially available operating system. The operator workstation 212 provides the operator interface that enables scanning control parameters to be entered into the CT system 200. In general, the operator workstation 212 is in communication with a data store server 220 and an image reconstruction system 222 through a communication system or network 224. By way of example, the operator workstation 212, data store sever 220, and image reconstruction system 222 may be connected via a communication system 224, which may include any suitable network connection, whether wired, wireless, or a combination of both. As an example, the communication system 224 may include both proprietary or dedicated networks, as well as open networks, such as the Internet.

The operator workstation 212 is also in communication with a control system 226 that controls operation of the CT system 200. The control system 226 generally includes an x-ray controller 228, a table controller 230, a gantry controller 231, and a data acquisition system (DAS) 232. The x-ray controller 228 provides power and timing signals to the x-ray module(s) 234 to effectuate delivery of the x-ray beam 236. The table controller 230 controls a table or platform 238 to position the subject 210 with respect to the CT system 200.

The DAS 232 samples data from the detector 208 and converts the data to digital signals for subsequent processing. For instance, digitized x-ray data is communicated from the DAS 232 to the data store server 220. The image reconstruction system 222 then retrieves the x-ray data from the data store server 220 and reconstructs an image there-from. The image reconstruction system 222 may include a commercially available computer processor, or may be a highly parallel computer architecture, such as a system that includes multiple-core processors and massively parallel, high-density computing devices. Optionally, image reconstruction can also be performed on the processor 218 in the operator workstation 212. Reconstructed images can then be communicated back to the data store server 220 for storage or to the operator workstation 212 to be displayed to the operator or clinician.

The CT system 200 may also include one or more networked workstations 240. By way of example, a networked workstation 240 may include a display 242; one or more input devices 244, such as a keyboard and mouse; and a processor 246. The networked workstation 240 may be located within the same facility as the operator workstation 212, or in a different facility, such as a different healthcare institution or clinic.

The networked workstation 240, whether within the same facility or in a different facility as the operator workstation 212, may gain remote access to the data store server 220 and/or the image reconstruction system 222 via the communication system 224. Accordingly, multiple networked workstations 240 may have access to the data store server 220 and/or image reconstruction system 222. In this manner, x-ray data, reconstructed images, or other data may be exchanged between the data store server 220, the image reconstruction system 222, and the networked workstations 212, such that the data or images may be remotely processed by a networked workstation 240. This data may be exchanged in any suitable format, such as in accordance with the transmission control protocol (TCP), the Internet protocol (IP), or other known or suitable protocols.

EXAMPLE

The above-described systems and methods were evaluated using two in vivo experiments conducted under the approval of our Institutional Animal Care and Use Committee (IACUC). Two adult beagles were studied. For each subject, an acute ischemic stroke model was created using an endovascular approach, and then a NCCT scan and a CTP perfusion scan were performed using a 64-slice, fixed-gantry CT scanner. The NCCT acquisition used 80 kV, automatic exposure control with a noise index (NI) of 3.4, helical mode, 0.5 s rotation time, and 40 mm beam collimation. The CTP acquisition used 80 kV, fixed mA (200 for Subject 1 and 100 for Subject 2), sequential axial (Cine) mode, 0.5 s rotation time, 40 mm beam collimation, a prep delay time of 5 s, a total acquisition time of 46 s, and a total of 23 time frames. To establish a reference for the location and volume of ischemic core, a diffusion-weighted imaging (DWI) was performed immediately after the CTP scan using a 3T MRI system.

After applying image registration and CT number bias correction, the NCCT image was combined with the CTP baseline images to obtain $I'_b(\vec{x})$ using Eqs. (10)-(11), and then a SVD-based delay insensitive deconvolution method with the Tichonov regularizer was used to estimate k and CBV.

The incorporation of the NCCT images to the CTP post-processing workflow effectively improved the quality of the CBV maps. For Subject 1, the noise standard deviation of CBV was reduced from 0.62 ml/100 g (without NCCT) to 0.43 ml/100 g (with NCCT), and the CNR of the core was improved from 3.0 to 4.9. For Subject 2, the noise standard deviation of CBV was reduced from 0.92 ml/100 g to 0.53 ml/100 g. The CNR was improved from 3.2 to 6.3. The noise reduction and CNR improvement effectively improved the visibility of the infarct territory. The existence of the infarction was confirmed by the DWI images.

The present invention has been described in terms of one or more preferred embodiments, and it should be appreciated that many equivalents, alternatives, variations, and modifications, aside from those expressly stated, are possible and within the scope of the invention.

The invention claimed is:

1. A medical imaging system comprising:
an x-ray source configured to deliver x-rays to an imaging patient;
a detector array configured to receive the x-rays after passing the imaging patient;
a controller configured to rotate the x-ray source and the detector array about the imaging patient as the x-ray source delivers the x-rays to the imaging patient and the detector array receives the x-rays;
a computer system configured to:
control operation of the x-ray source and the detector array to perform a non-contrast computed tomography (NCCT) imaging acquisition to acquire NCCT data;
control operation of the x-ray source and the detector array to perform a computed tomography perfusion (CTP) imaging acquisition to acquire CTP data;
create a baseline image using the NCCT data;
generate a parametric map using the CTP data and the baseline image; and
wherein the computer system is further configured to create the baseline image by fusing the NCCT data with the CTP data.

2. The system of claim 1 wherein the computer system is further configured to select a baseline frame from the CTP data and fuse the baseline frame from the CTP data with at least one image frame from the NCCT data to generate the baseline image.

3. The system of claim 2 wherein the computer system is further configured to fuse the baseline frame from the CTP data with the NCCT data by:

$$I'_b = wI_{NCCT} + (1-w)I_b,$$

where $I_{NCCT}$ is the NCCT data, $I_b$ is the baseline frame from the CTP data, and w is a weighting factor chosen to control the noise variance of $I'_b$.

4. The system of claim 3 wherein the computer system is further configured to choose w using $\arg\min_w \{w^2\sigma_{NCCT}^2 + (1-w)^2\sigma_b^2\}$, wherein $\sigma_{NCCT}^2$ denotes noise variance of the NCCT data, and $\sigma_b^2$ denotes the noise variance of the baseline image.

5. The system of claim 3 wherein the computer system is further configured to generate the parametric map using a portion of the CTP data acquired after the baseline frame from the CTP data.

6. The system of claim 5 wherein the computer system is further configured to generate the parametric map using a portion of the CTP data acquired after the baseline frame from the CTP data.

7. The system of claim 1 wherein the parametric map includes a cerebral blood volume (CBV) map.

8. The system of claim 1 wherein the CTP data includes contrast-enhanced image data of a brain of the patient.

9. A method for generating a parametric map of a subject's brain, the method comprising:

receiving non-contrast computed tomography (NCCT) imaging data;
receiving computed tomography perfusion (CTP) data;
creating a baseline image using the NCCT data;
generating a parametric map using the CTP data and the baseline image; and
wherein creating the baseline image by fusing the NCCT data with the CTP data.

10. The method of claim 9 further comprising selecting a baseline frame from the CTP data and fusing the baseline image frame from the CTP data with at least one image frame from the NCCT data to generate the baseline image.

11. The method of claim 10 wherein fusing the baseline frame from the CTP data with the at least one mage frame from the NCCT data is performed according to:

$$I'_b = wI_{NCCT} = (1-w)I_b,$$

where $I_{NCCT}$ is the at least one mage frame from the NCCT data, $I_b$ is the baseline frame from the CTP data, and w is a weighting factor chosen to control the noise variance of $I'_b$.

12. The method of claim 11 further comprising choose w using:

$$\arg\min_w \{w^2 \sigma_{NCCT}^2 + (1-w)^2 \sigma_b^2\},$$

wherein $\sigma_{NCCT}^2$ denotes noise variance of the NCCT data used to create the baseline image, and $\sigma_b^2$ denotes the noise variance of the baseline image.

13. The method of claim 11 wherein generating the parametric map includes using a portion of the CTP data acquired after the baseline frame from the CTP data.

14. The method of claim 13 wherein generating the parametric map includes using a portion of the CTP data acquired after the baseline frame from the CTP data.

15. The method of claim 9 wherein the parametric map includes a cerebral blood volume (CBV) map.

16. The method of claim 9 wherein the CTP data includes contrast-enhanced image data of a brain of the patient.

17. A computer system configured to generate a parametric map of a subject's brain, the computer system comprising:
a non-transitory tangible memory storing non-contrast computed tomography (NCCT) imaging data acquired from the subject and computed tomography perfusion (CTP) data acquired from the subject;
a processor having access to the memory and configured to:
create a baseline image using the NCCT data;
generate a parametric map using the CTP data and the baseline image; and
wherein the processor is further configured to create the baseline image by fusing the NCCT data with a portion of the CTP data.

* * * * *